United States Patent
Cyprowski

(10) Patent No.: US 10,483,778 B2
(45) Date of Patent: Nov. 19, 2019

(54) BATTERY SYSTEM WITH LOW POWER MODE

(71) Applicant: KONINKLIJKE PHILIPS N.V., Eindhoven (NL)

(72) Inventor: Ronald Cyprowski, Pittsburgh, PA (US)

(73) Assignee: Koninklijke Philips N.V., Eindhoven (NL)

(*) Notice: Subject to any disclaimer, the term of this patent is extended or adjusted under 35 U.S.C. 154(b) by 59 days.

(21) Appl. No.: 15/578,730

(22) PCT Filed: May 12, 2016

(86) PCT No.: PCT/IB2016/052711
§ 371 (c)(1),
(2) Date: Dec. 1, 2017

(87) PCT Pub. No.: WO2016/193838
PCT Pub. Date: Dec. 8, 2016

(65) Prior Publication Data
US 2018/0175649 A1    Jun. 21, 2018

Related U.S. Application Data

(60) Provisional application No. 62/170,295, filed on Jun. 3, 2015.

(51) Int. Cl.
*H02J 7/00* (2006.01)
*A61M 16/00* (2006.01)
*H01M 10/44* (2006.01)

(52) U.S. Cl.
CPC ....... *H02J 7/0063* (2013.01); *A61M 16/0003* (2014.02); *H01M 10/44* (2013.01); *H02J 7/0029* (2013.01); *H02J 7/0031* (2013.01); *A61M 2016/0027* (2013.01); *A61M 2205/8206* (2013.01); *H02J 2007/0067* (2013.01)

(58) Field of Classification Search
CPC .. A61M 16/0003; H02J 7/0029; H02J 7/0031; H02J 7/0047; H02J 7/0063; H02J 2007/0067
USPC .................................. 307/31, 116, 125, 126
See application file for complete search history.

(56) References Cited

U.S. PATENT DOCUMENTS

| | | | |
|---|---|---|---|
| 6,208,117 B1 | 3/2001 | Hibi | |
| 2006/0076934 A1* | 4/2006 | Ogata | H02J 7/0031 320/136 |
| 2009/0146826 A1 | 6/2009 | Gofman | |
| 2010/0146318 A1 | 6/2010 | Johnson | |

(Continued)

OTHER PUBLICATIONS

"bq27742-G1 Single-Cell Impedance Tracklm Battery Fuel Gauge With Programmable Hardware Protection", Technical Reference Manual, Texas Instruments, Mar. 2014—Revised Dec. 2014.

*Primary Examiner* — William Hernandez
(74) *Attorney, Agent, or Firm* — Michael W. Haas

(57) ABSTRACT

Systems and methods for controlling transitions between a low power mode of operation and a functional mode of operation of a battery system use power provided by the battery cell in the battery system to cause the transitions. The battery system includes a status circuit, a charge/discharge circuit, a set of battery ports, and/or other components. During the low power mode of operation, at least the charge/discharge circuit is rendered inoperative, thus saving power.

15 Claims, 4 Drawing Sheets

(56) References Cited

U.S. PATENT DOCUMENTS

2012/0203178 A1 8/2012 Tverskoy
2013/0314047 A1 11/2013 Eagle

* cited by examiner

BATTERY SYSTEM WITH LOW POWER MODE

CROSS-REFERENCE TO RELATED APPLICATIONS

This patent application claims the priority benefit under 35 U.S.C. § 371 of international patent application no. PCT/IB2016/052711, filed May 12, 2016, which claims the priority benefit under 35 U.S.C. § 119(e) of U.S. Provisional Application No. 62/170,295, filed on Jun. 3, 2015, the contents of which are herein incorporated by reference.

BACKGROUND OF THE INVENTION

1. Field of the Invention

The present disclosure pertains to a system and method for controlling transitions between a low power mode of operation of a battery system and a functional mode of operation of the battery system, and, in particular, to using power provided by the battery system itself to cause a transition from a low power mode to a functional mode.

2. Description of the Related Art

Some types of battery systems slowly leak power when not in use. Common battery systems are configured to operate in one of multiple modes of operation. The modes of operation may include one or more low power modes of operation when the battery system is not being used to provide power to an external circuit or electrical load (e.g. a medical device), one or more functional modes of operation during which the battery system provides power to the external circuit or electrical load, and/or other modes of operation. Due to power/current leakage, battery systems commonly have a limited shelf life of usability between periods of being charged. Some battery systems require an external source of power, for example power provided through an outlet to cause a transition in the battery system from a low power mode of operation to a functional mode of operation.

SUMMARY OF THE INVENTION

One embodiment of the present disclosure provides a battery system constructed and arranged to control transitions between a low power mode of operation during which the battery system is configured to preserve energy and a functional mode of operation during which the battery system is configured to provide energy to one or more external circuits. The one or more external circuits are external to the battery system and include an electrical load and a switchable circuit. The battery system comprises a set of battery ports, a battery cell, a discharge circuit, and a status circuit. The set of battery ports is configured to operatively couple the battery system to the one or more external circuits. The set of battery ports includes a first battery port and a second battery port. The first battery port is configured to operatively couple the battery system to the electrical load during the functional mode of operation. The second battery port is configured to operatively couple the battery system to the external switchable circuit during the low power mode of operation. The switchable circuit is related to the electrical load. The battery cell is configured to provide energy to the first battery port and the second battery port. The discharge circuit is configured to provide a coupling between the battery cell and the first battery port. The discharge circuit is further configured such that the coupling is operative during an operative state of the discharge circuit. The discharge circuit is further configured such that the coupling is inoperative during an inoperative state of the discharge circuit. The status circuit is configured to selectively operate in the low power mode of operation or the functional mode of operation. The status circuit is further configured to cause the discharge circuit to be in the inoperative state responsive to the status circuit operating in the low power mode of operation. The status circuit is further configured to cause the discharge circuit to be in the operative state responsive to provision of energy from the battery cell, through the second battery port, through the switchable circuit, through an individual battery port in the set of battery ports, to the status circuit.

Other embodiments of the present disclosure provide a method for controlling transitions of a battery system between a low power mode of operation during which the battery system preserves energy and a functional mode of operation during which the battery system provides energy to one or more external circuits. The one or more external circuits are external to the battery system and include an electrical load and a switchable circuit. The method is implemented in a battery system including a battery cell, a set of battery ports, a discharge circuit, and a status circuit. The set of battery ports includes a first battery port and a second battery port. The method comprises: operatively coupling, through the first battery port, the battery system to the electrical load during the functional mode of operation such that the battery cell provides energy to the electrical load; operatively coupling, through the second battery port, the battery system to the switchable circuit during the low power mode of operation such that the battery cell provides energy to the switchable circuit, wherein the switchable circuit is related to the electrical load; providing energy, by the battery cell, to the first battery port and the second battery port; providing, by the discharge circuit, a coupling between the battery cell and the first battery port such that the coupling is operative during an operative state of the discharge circuit, and such that the coupling is inoperative during an inoperative state of the discharge circuit; and selectively operating, by the status circuit, in the low power mode of operation or the functional mode of operation such that, responsive to the status circuit operating in the low power mode of operation, the status circuit causes the discharge circuit to be in the inoperative state, and further such that, responsive to provision of energy from the battery cell, through the second battery port, through the switchable circuit, through an individual battery port in the set of battery ports, to the status circuit, the status circuit causes the discharge circuit to be in the operative state.

Yet another embodiment of this disclosure provides a battery system constructed and arranged to control transitions between a low power mode of operation during which the battery system preserves energy and a functional mode of operation during which the battery system provides energy to one or more external circuits. The one or more external circuits are external to the battery system and include an electrical load and a switchable circuit. The battery system comprises a set of coupling means, an energy means, a discharge means, and a status means. The set of coupling means for operatively coupling the battery system to the one or more external circuits includes a first coupling means and a second coupling means. The first coupling means for operatively coupling the battery system to the electrical load during the functional mode of operation is configured to operate such that the battery cell provides energy to the electrical load through the discharge circuit. The second coupling means for operatively coupling the battery system to the switchable circuit during the low power mode of operation is configured to operate such that the battery cell provides energy to the switchable circuit bypassing the discharge circuit, wherein the switchable circuit is related to the electrical load. The energy means for providing energy is configured to provide energy to the first coupling means and the second coupling means. The discharge means for providing a coupling between the battery cell and the first battery port is configured to operate such that the coupling is operative during an operative state of the discharge means, and is further configured to operate such that the coupling is inoperative during an inoperative state of the discharge means. The status means for selectively operating in the low power mode of operation or the functional mode of operation is configured to operate such that, responsive to the status means operating in the low power mode of operation, the status means is configured to cause the discharge means to be in the inoperative state, and further such that, responsive to provision of energy from the energy cell, through the second coupling means, through the switchable circuit, through an individual coupling means in the set of coupling means, to the status means, the status means is configured to cause the discharge means to be in the operative state.

These and other, features, aspects and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
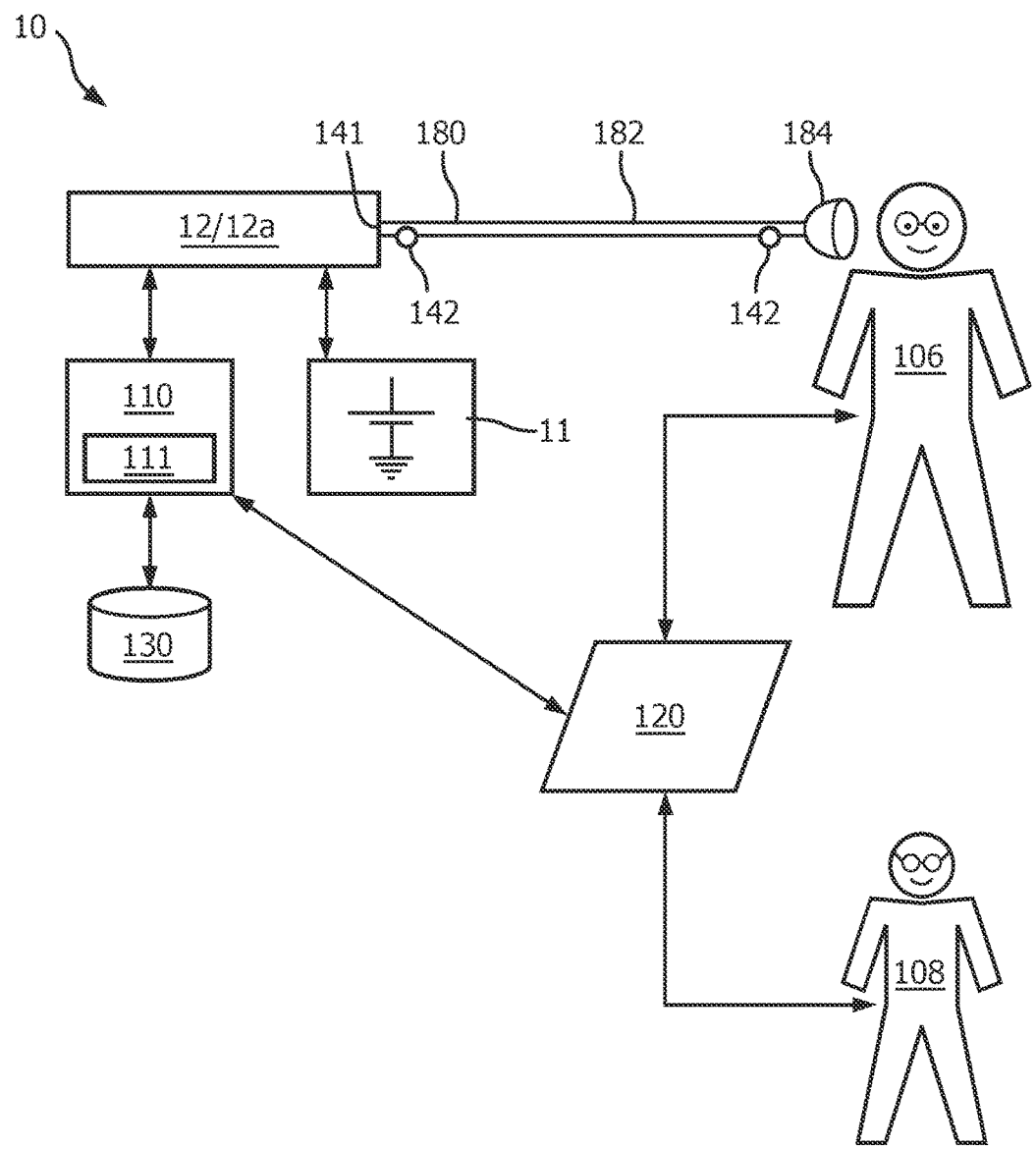
FIG. 1 schematically illustrates an exemplary system that includes a battery system in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary system 10 that includes a battery system 11. System 10 may include, be implemented as, integrated with, and/or operate in conjunction with a medical device 12. Medical device 12 may be configured to use battery system 11 to provide power to medical device 12. In some embodiments, medical device 12 may be configured to operate using power provided by an outlet and/or battery system 11. For example, battery system 11 may act as a backup battery to provide power to medical device 12 in case the power from an outlet fails, is discontinued, is disconnected, and/or is otherwise unavailable. In some embodiments, medical device 12 may include one or more of a respiratory therapy device, a ventilator, a pressure generator, an airway pressure device, and/or other medical devices that require power to operate.

By way of non-limiting example, FIG. 1 illustrates a medical device 12 that includes one or more of a pressure generator 12a, a delivery circuit 180, one or more sensors 142, an electronic storage 130, a user interface 120, a processor 110, a control component 111, a battery system 11, and/or other components. Battery system 11, medical device 12, and/or system 10 may be used by a subject 106 and/or for the benefit of subject 106. For example, subject 106 may be a patient. In some embodiments, battery system 11, medical device 12, and/or system 10 may be used by a user 108 related to subject 106. For example, user 108 may be a caregiver, a therapy decision-maker, a medical professional, staff or personnel in a care facility or medical facility, and/or another user.

Figure 3A:
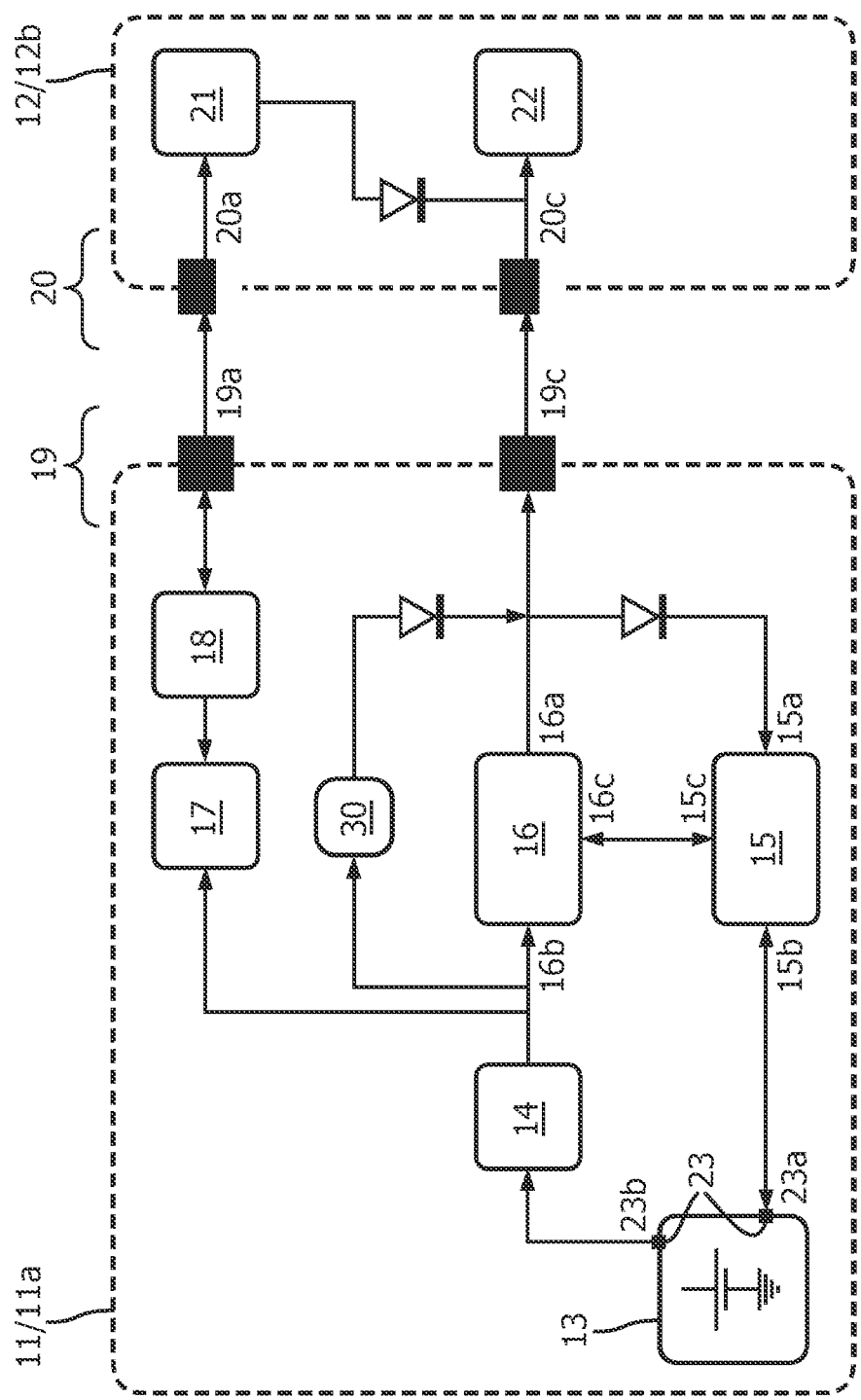
FIG. 3A schematically illustrates a battery system having at least two battery ports in accordance with one or more embodiments.
Figure 3B:
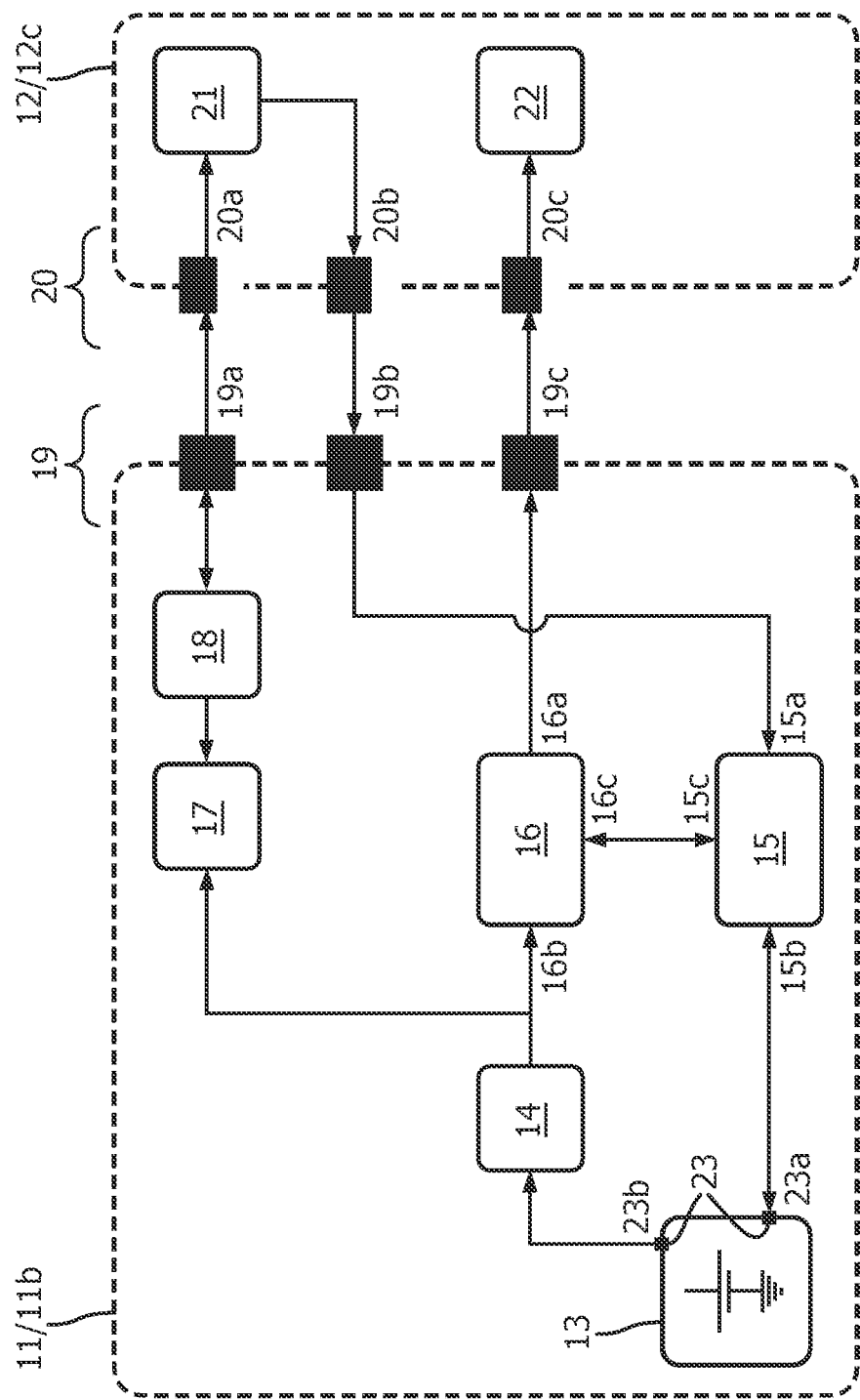
FIG. 3B schematically illustrates a battery system having at least three battery ports in accordance with one or more embodiments.

Referring to FIG. 3A and FIG. 3B, battery system 11 may include one or more of a battery cell 13 (or multiple battery cells 13), a set of battery ports 19, a status circuit 15, a discharge circuit 16, a protection device 14, a current limit device 17, a blocking device 18, an internal switchable circuit 30, and/or other components. Embodiments of battery system 11 may be referred to as battery system 11a in FIG. 3A and battery system 11b in FIG. 3B. Embodiments of medical device 12 may be referred to as medical device 12a in FIG. 1, medical device 12b in FIG. 3A, and medical device 12c in FIG. 3B. In some embodiments, battery system 11 may include at least two battery ports, as illustrated in FIG. 3A. In some embodiments, battery system 11 may include at least three battery ports, as illustrated in FIG. 3B. Set of battery ports 19 may include one or more of first battery port 19c, second battery port 19a, third battery port 19b, and/or other battery ports. Illustration of components in FIG. 3A is not intended to limit inclusion of such components in FIG. 3B, nor vice versa. Any combination of illustrated components is envisioned within the scope of this disclosure. Any combination of components described in this disclosure is envisioned.

Referring to FIG. 3A and FIG. 3B, battery system 11 may be configured to operate in different modes of operation. In some embodiments, battery system 11 may be configured to transition between different modes of operation. The modes of operation may include one or more low power modes of operation, one or more functional modes of operation, and/or other modes of operation. During the one or more low power modes of operation, battery system 11 may be configured to preserve power and/or not provide power to external devices. During the one or more low power modes of operation, the discharge currents of battery system 11 may be multiple orders of magnitude smaller than the typical discharge current during a functional mode of operation, e.g. active usage of medical device 12. A transition of battery system 11 from a low power mode of operation to a functional mode of operation may be referred to as "waking up."

In some embodiments, external devices may include one or more of medical device 12, an electrical load 22, a switchable circuit 21, and/or other external circuits that are external to battery system 11 (and or circuits that are external or beyond set of battery ports 19 of battery system 11), and/or any combinations thereof. During the one or more functional modes of operation, battery system 11 may be configured to provide power to external devices. In some embodiments, battery system 11 may be configured to use multiple low power modes of operation. For example, the low power modes of operation may include a low power sleep mode, a low power shutdown mode, and/or other low power modes. By virtue of the features described in this disclosure, the rate of depletion of energy contained within battery system 11 during an individual one of the one or more low power modes of operation may be reduced in comparison to currently available battery systems. In some embodiments, the rate of depletion may be independent of the presence or absence of an external device that is operatively connected to battery system 11. Alternatively, and/or simultaneously, by virtue of the features described in this disclosure, the power used to cause a transition of battery system 11 from a low power mode of operation to a functional mode of operation may be provided by battery system 11 itself, in contrast to some currently available battery systems that require power to be provided by an external power source for this purpose. In other words, battery system 11 may provide the power to wake itself up.

In some embodiments, battery system 11*a* may include internal switchable circuit 30. For example, internal switchable circuit may be implemented as a capacity switch. Internal switchable circuit 30 may include at least two terminals. In some embodiments, internal switchable circuit 30 may include one or more of a mechanical switch, a latch, a zero-current latch, and/or other types of circuitry that selectively provide an electrical coupling between different parts or sections of an electrical system. For example, internal switchable circuit 30 may be configured to be open or closed, on or off, operative or inoperative, and so forth. In response to internal switchable circuit 30 being closed, activated, turned on, and/or otherwise rendered operative such that a first terminal of internal switchable circuit 30 is operatively coupled with a second terminal of internal switchable circuit 30, at least some portion and/or functionality of status circuit 15 may be activated. For example, one or more indicators representing the current capacity (and/or other status information) of battery cell 13 may be activated and/or functional. In some embodiments, in response to internal switchable circuit 30 being closed, activated, turned on, and/or otherwise rendered operative, battery system 11 and/or components thereof may transition, e.g. temporarily, from a low power mode of operation to a functional mode of operation. In some embodiments, status circuit 15 may be configured to automatically revert such a transition, e.g. after a time-out (e.g. the expiration of a predetermined period of time).

In some embodiments, medical device 12*b* may include a switchable circuit 21, an electrical load 22, a set of device ports 20, and/or other components. As illustrated in FIG. 3A, medical device 12*b* may include a first device port 20*a* and a second device port 20*c*. First device port 20*a* may operatively couple to switchable circuit 21. Second device port 20*c* may operatively couple to electrical load 22. Switchable circuit 21 may operatively couple to second device port 20*c*, e.g. through a diode or other electronic component having asymmetric conductance.

In some embodiments, medical device 12*c* may include switchable circuit 21, electrical load 22, set of device ports 20, and/or other components. As illustrated in FIG. 3B, medical device 12*c* may include a first device port 20*a*, a second device port 20*c*, and a third device port 20*b*. First device port 20*a* may operatively couple to switchable circuit 21. Switchable circuit 21 may operatively couple to third device port 20*b*. Second device port 20*c* may operatively couple to electrical load 22.

Status circuit 15 may be configured to monitor and/or report status information of battery system 11 and/or battery cell 13. In some embodiments, status circuit 15 may be referred to as the fuel gauges of battery system 11 and/or battery cell 13. The status information may include parameters related to one or more of a capacity, current, voltage, temperature, safety status, permanent fail status, and/or other status information related to battery system 11 and/or battery cell 13. Status circuit 15 may be configured to periodically sample, gather, measure, and/or otherwise obtain information from battery cell 13, e.g. status information. In some modes of operation of battery system 11, power consumption by status circuit 15 may be reduced, e.g. by no longer providing power to at least a portion of status circuit 15. In some embodiments, power consumption by status circuit 15 may be reduced to a current leakage of about 10 micro-amps, about 5 micro-amps, about 4 micro-amps, about 3 micro-amps, about 2 micro-amps, about 1 micro-amp, less than 1 micro-amp, and/or another level of current leakage.

In some embodiments, status information may be obtained through a System Management Bus (SMBus) serial communication interface, and/or another communication interface.

Battery cell 13 may include one or more "N cells", a set of battery cell ports 23, and/or other components. Battery cell 13 may be configured to store energy, to provide energy, and/or provide the ability to be charged and/or discharged. Set of battery cell ports 23 may include a first battery cell port 23*b*, a second battery cell port 23*a*, and/or other battery cell ports. In some embodiments, second battery cell port 23*a* may be operatively coupled to status circuit 15. In some embodiments, first battery cell port 23*b* may be operatively coupled to an individual one of set of battery ports 19. For example, first battery cell port 23 b may be operatively coupled, via protection device 14 and discharge circuit 16, to first battery port 19*c*. For example, first battery port 23*b* may be operatively coupled, via protection device 14, current limit device 17, and blocking device 18, to second battery port 19*a*.

Status circuit 15 may include a set of connectors. In some embodiments, for example as illustrated in FIGS. 3A-3B, the set of connectors may include a first connector 15*a*, a second connector 15*b*, a third connector 15*c*, and/or other connectors. For example, first connector 15*a* may be operatively coupled to an individual one of set of battery ports 19. In some embodiments, first connector 15*a* may be operatively coupled to first battery port 19*c*, as illustrated for battery system 11*a* in FIG. 3A. In some embodiments, first connector 15*a* may be operatively coupled to third battery port 19*b*, as illustrated for battery system 11*b* in FIG. 3B. Second connector 15*b* may be operatively coupled to an individual one of set of battery cell ports 23, for example for communication of status information. Third connector 15*c* may be operatively coupled to discharge circuit 16, for example such that status circuit 15 causes a particular state of discharge circuit 16 and/or controls discharge circuit 16.

Discharge circuit 16 may be configured to provide a coupling between battery cell 13 and an individual one of set of battery ports 19, e.g. for the purpose of providing energy form battery cell 13 to an external device. In some embodiments, discharge circuit 16 may include one or more transistors, for example field effect transistors or FETs. In some embodiments, these FETs may be referred to as charge/discharge FETs. In some embodiments, discharge circuit 16 may operate in different states. By way of non-limiting example, the different states may include an operative state, an inoperative state, and/or other states. In some embodiments, discharge circuit 16 may be configured such that the coupling is operative during an operative state of discharge circuit 16. For example, power may be provided to and/or consumed by the charge/discharge FETs during the operative state. In some embodiments, discharge circuit 16 may be configured such that the coupling is inoperative during an inoperative state of discharge circuit. For example, power may be not provided to and/or not consumed by the charge/discharge FETs during the inoperative state. For example, less power may be provided to and/or consumed by the charge/discharge FETs during the inoperative state, in comparison to the operative state. In some embodiments, power consumption by discharge circuit 16 may be reduced to a current leakage of about 10 micro-amps, about 5 micro-amps, about 4 micro-amps, about 3 micro-amps, about 2 micro-amps, about 1 micro-amp, less than 1 micro-amp, and/or another level of current leakage.

In some embodiments, the operative state of discharge circuit 16 may correspond to a functional mode of operation of battery system 11. In some embodiments, the inoperative state of discharge circuit 16 may correspond to a low power mode of operation of battery system 11. As used herein, a correspondency between the state of discharge circuit 16 and the mode of operation of battery system 11 may refer to transitions between states occurring simultaneously or nearly at the same time as transitions between modes of operation. For example, a transition in the mode of operation of battery system 11 may cause a transition in the state of discharge circuit 16, and/or vice versa. For example, an occurrence and/or event that causes a transition in the mode of operation of battery system 11 may cause a transition in the state of discharge circuit 16, and/or vice versa. By virtue of the features described in this disclosure, power consumption by discharge circuit 16 may be reduced, e.g. during a low power mode of operation of battery system 11, by causing discharge circuit 16 to be in the inoperative state.

As used herein, discharge circuit 16 may also be referred to as charge/discharge circuit 16. Charge/discharge circuit 16 may be configured to provide a coupling from an individual one of set of battery ports 19 and battery cell 13, e.g. for the purpose of charging battery cell 13.

Discharge circuit 16 may include a set of connectors. In some embodiments, for example as illustrated in FIGS. 3A-3B, the set of connectors may include a first connector 16*a*, a second connector 16*b*, a third connector 16*c*, and/or other connectors. For example, first connector 16*a* may be operatively coupled to an individual one of set of battery ports 19, such as first battery port 19*c*. For example, second connector 16*b* may be operatively coupled, e.g. via protection device 14, to an individual one of set of battery cell ports 23, such as first battery cell port 23*b*. For example, third connector 16*c* may be operatively coupled to status circuit 15, for example to third connector 15*c*.

Protection device 14 may be configured to protect battery cell 13 from electrical signals, currents, and/or voltages that may harm battery cell 13. In some embodiments, protection device 14 may include two terminals. A first terminal may be operatively connected to battery cell 13 (e.g. through an individual battery cell port in set of battery cell ports 23). A second terminal may be operatively connected to discharge circuit 16 (e.g. through second connector 16*b*). Alternatively, and/or simultaneously, in some embodiments, a second terminal may be operatively connected to current limit device 17.

Current limit device 17 may include at least two terminals. Current limit device may be configured to limit the current flowing from a first terminal to a second terminal. The first terminal may be operatively coupled to one or both of the second terminal of protection device 14 and an individual battery cell port in set of battery cell ports 23. The second terminal may be operatively coupled to blocking device 18.

Blocking device 18 may include at least two terminals. Blocking device 18 may be configured to block and/or limit the current flowing in a particular direction through its first terminal and second terminal. In some embodiments, blocking device 18 may include a diode and/or another electronic component having asymmetric conductance. The first terminal may be operatively coupled to current limit device 17. The second terminal may be operatively coupled to an individual one of set of battery ports 19, such as second battery port 19*a*.

Switchable circuit 21 may include at least two terminals. In some embodiments, switchable circuit 21 may include one or more of a mechanical switch, a latch, a zero-current latch, and/or other types of circuitry that selectively provide an electrical coupling between different parts or sections of an electrical system. For example, switchable circuit 21 may be configured to be open or closed, on or off, operative or inoperative, and so forth.

Referring to FIG. 3A, battery system 11*a* may be configured to operate in a low power mode of operation, e.g. in response to an external device causing, through set of battery ports 19, one or both of status circuit 15 and discharge circuit 16 to reduce power consumption in comparison to a functional mode of operation during which battery system 11*a* provides power to one or more external circuits, e.g. active usage of medical device 12*b*. In some embodiments, status circuit 15 may be configured to operate in different modes of operation, for example corresponding to the modes of operation of battery system 11*a*. In some embodiments, status circuit 15 may be configured to be controlled and/or programmed, e.g. through first battery port 19*c* and/or set of connectors 15, to cause a particular mode of operation and/or a particular transition between different modes of operation. In some embodiments, a first low power mode of operation may be referred to as a low power sleep mode. During the low power sleep mode of operation, power consumption of discharge circuit 16 may be reduced, e.g. by no longer providing power to at least a portion of discharge circuit 16 and/or by causing discharge circuit 16 to be in an inoperative state. In some embodiments, a second low power mode of operation may be referred to as a low power shutdown mode. During the low power shutdown mode of operation, power consumption of both discharge circuit 16 and status circuit 15 may be reduced, e.g. by no longer providing power to at least a portion of discharge circuit 16 and status circuit 15 and/or by causing discharge circuit 16 to be in an inoperative state and status circuit 15 is in a low power mode of operation.

Referring to FIG. 3A, battery system 11a may be configured to transition from a low power mode of operation to a functional mode of operation, e.g. in response to an action or event from an external device. For example, such a transition may occur in response to switchable circuit 21 being closed, activated, turned on, and/or otherwise rendered operative such that a first terminal of switchable circuit 21 is operatively coupled with a second terminal of switchable circuit 21. As illustrated in FIG. 3A, the first terminal of switchable circuit 21 may be operatively coupled to first device port 20a, second battery port 19a, blocking device 18, current limit device 17, protection device 14, and battery cell 13. The second terminal of switchable circuit 21 may be operatively coupled to second device port 20c, first battery port 19c, a diode, and first connector 15a of status circuit 15. In response to switchable circuit 21 being closed, activated, turned on, and/or otherwise rendered operative, power provided by battery cell 13 may, via protection device 14, current limit device 17, blocking device 18, second battery port 19a, first device port 20a, switchable circuit 21, second device port 20c, first battery port 19c, and first connector 15a, cause a transition by status circuit 15 from a low power mode of operation to a functional mode of operation. In response to such a transition, status circuit 15 may cause discharge circuit 16 to be in an operate state. Subsequent to that response, battery system 11a may be in a functional mode of operation, during which power provided by battery cell 13, through protection device 14, discharge circuit 16, and first battery port 19c, is provided to one or more external circuits, e.g. medical device 12b (and/or electrical load 22).

Referring to FIG. 3B, battery system lib may be configured to operate in a low power mode of operation, e.g. in response to an external device causing, through set of battery ports 19, one or both of status circuit 15 and discharge circuit 16 to reduce power consumption in comparison to a functional mode of operation during which battery system 11b provides power to one or more external circuits, e.g. active usage of medical device 12c. In some embodiments, status circuit 15 may be configured to operate in different modes of operation, for example corresponding to the modes of operation of battery system lib. In some embodiments, status circuit 15 may be configured to be controlled and/or programmed, e.g. through first battery port 19c and/or set of connectors 15, to cause a particular mode of operation and/or a particular transition between different modes of operation. In some embodiments, a first low power mode of operation may be referred to as a low power sleep mode. During the low power sleep mode of operation, power consumption of discharge circuit 16 may be reduced, e.g. by no longer providing power to at least a portion of discharge circuit 16 and/or by causing discharge circuit 16 to be in an inoperative state. In some embodiments, a second low power mode of operation may be referred to as a low power shutdown mode. During the low power shutdown mode of operation, power consumption of both discharge circuit 16 and status circuit 15 may be reduced, e.g. by no longer providing power to at least a portion of discharge circuit 16 and status circuit 15 and/or by causing discharge circuit 16 to be in an inoperative state and status circuit 15 is in a low power mode of operation.

Referring to FIG. 3B, battery system lib may be configured to transition from a low power mode of operation to a functional mode of operation, e.g. in response to an action or event from an external device. For example, such a transition may occur in response to switchable circuit 21 being closed, activated, turned on, and/or otherwise rendered operative such that a first terminal of switchable circuit 21 is operatively coupled with a second terminal of switchable circuit 21. As illustrated in FIG. 3B, the first terminal of switchable circuit 21 may be operatively coupled to first device port 20a, second battery port 19a, blocking device 18, current limit device 17, protection device 14, and battery cell 13. The second terminal of switchable circuit 21 may be operatively coupled to third device port 20b, third battery port 19b, and first connector 15a of status circuit 15. In response to switchable circuit 21 being closed, activated, turned on, and/or otherwise rendered operative, power provided by battery cell 13 may, via protection device 14, current limit device 17, blocking device 18, second battery port 19a, first device port 20a, switchable circuit 21, third device port 20b, third battery port 19b, and first connector 15a, cause a transition by status circuit 15 from a low power mode of operation to a functional mode of operation. In response to such a transition, status circuit 15 may cause discharge circuit 16 to be in an operate state. Subsequent to that response, battery system lib may be in a functional mode of operation, during which power provided by battery cell 13, through protection device 14, discharge circuit 16, and first battery port 19c, is provided to one or more external circuits, e.g. medical device 12c (and/or electrical load 22).

In some embodiments, battery system 11a may be combined with medical device 12c. In some embodiments, battery system lib may be combined with medical device 12b.

First battery port 19c may be configured to operatively couple battery system 11 during a functional mode of operation to one or more external circuits, e.g. electrical load 22 of medical device 12. In some embodiments, first battery port 19c may be configured to operatively couple battery cell 13 during a functional mode of operation to one or more external circuits, e.g. electrical load 22 of medical device 12.

Second battery port 19a may be configured to operatively couple battery system 11 during a low power mode of operation to switchable circuit 21. In some embodiments, second battery port 19a may be configured to operatively couple battery cell 13 during a low power mode of operation to switchable circuit 21.

Third battery port 19b may be configured to indicate whether an external circuit is present or absent, e.g. electrical load 22 of medical device 12. For example, provision of energy, a particular current, and/or a particular voltage through third battery port 19b may indicate presence or absence of an external circuit. In some embodiments, third battery port 19b may be configured to indicate whether an external circuit is active or inactive, e.g. electrical load 22 of medical device 12. For example, provision of energy, a particular current, and/or a particular voltage through third battery port 19b may indicate that an external circuit is active or inactive.

In some embodiments, the mode of operation of status circuit 15 may correspond to a functional mode of operation of battery system 11. In some embodiments, a low power mode of operation of status circuit 15 may correspond to a low power mode of operation of battery system 11. As used herein, a correspondency between the mode of operation of status circuit 15 and the mode of operation of battery system 11 may refer to transitions between modes of operation occurring simultaneously or nearly at the same time. For example, a transition in the mode of operation of battery system 11 may cause a transition in the mode of operation of status circuit 15, and/or vice versa. For example, an occurrence and/or event that causes a transition in the mode of operation of battery system 11 may cause a transition in the mode of operation of status circuit 15, and/or vice versa.

In some embodiments, the mode of operation of status circuit 15 may not correspond to a functional mode of operation of battery system 11. For example, status circuit 15 may operate in a functional mode of operation while battery system 11 operates in a low power mode of operation. In this example, transitions between modes of operation may not need to occur simultaneously or nearly at the same time.

Referring to FIG. 1, medical device 12 may include a pressure generator 12a. Battery system 11 may be configured to provide power to pressure generator 12a, and/or other components of system 10. Pressure generator 12a of system 10 in FIG. 1 may be integrated, combined, coupled, and/or connected with a (positive) airway pressure device (PAP/CPAP/BiPAP®/etc.). Pressure generator 12a may be configured to provide a pressurized flow of breathable gas for delivery to the airway of subject 106, e.g. via an output 141 of pressure generator 12a, and/or via a delivery circuit 180. Delivery circuit 180 may be referred to as subject interface 180. In some embodiments, subject 106 may initiate one or more phases of respiration. In some embodiments, subject 106 may not initiate any phases of respiration. Respiratory therapy may be implemented as pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Adjustments may be made numerous times in implementations using auto-titrating for providing respiratory support through the delivery of the pressurized flow of breathable gas. In addition to alternating between multiple levels, the inhalation pressure level may ramp up or down according to a predetermined slope (absolute and/or relative, e.g. dependent on breathing rate) for any specified section of a phase. Similar features may be available for exhalation phases. The pressure levels may be either predetermined and fixed, follow a predetermined dynamic characteristic, or they may dynamically change breath-to-breath or night-to-night depending on sensed breathing, breathing disorder, or other physiological characteristics. Pressure generator 12a may be configured to adjust one or more of pressure levels, flow, humidity, velocity, acceleration, and/or other parameters of the pressurized flow of breathable gas, e.g. in substantial synchronization with the breathing cycle of the subject.

An airway pressure device may be configured such that one or more gas parameters of the pressurized flow of breathable gas are controlled in accordance with a therapeutic respiratory regimen for subject 106. The one or more gas parameters include one or more of flow, volume, retrograde volume, pressure, humidity, velocity, acceleration, (intentional) gas leak, and/or other parameters. System 10 may be configured to provide types of therapy including types of therapy where a subject performs inspiration and/or expiration of his own accord or where the device provides negative airway pressure.

Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 12a. Conduit 182 may form a flow path through which the pressurized flow of breathable gas is communicated between subject interface appliance 184 and pressure generator 12a.

Subject interface appliance 184 of system 10 in FIG. 1 may be configured to deliver the pressurized flow of breathable gas to the airway of subject 106. As such, subject interface appliance 184 may include any appliance suitable for this function. In some embodiments, pressure generator 12a may be a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Electronic storage 130 of system 10 in FIG. 1 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, FRAM, etc.), solid-state storage media (e.g., flash drive, etc.), and/or other electronically readable storage media. Electronic storage 130 may store software algorithms, information determined by processor 110, information received via user interface 120, and/or other information that enables system 10 and/or battery system 11 to function properly. For example, electronic storage 130 may record or store status information, timing information (including duration of inhalation phases and exhalation phases as well as transitional moments), one or more (breathing) parameters and/or other parameters (as discussed elsewhere herein), pressure levels, pressure drop estimated at various moments, information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, information indicating adequacy of treatment, and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed to user 108 is a report detailing the performance of battery system 11 throughout a particular period, e.g. during which the subject is receiving therapy. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

One or more sensors 142 of system 10 in FIG. 1 are configured to generate output signals conveying measurements related to gas parameters of respiratory airflow, parameters related to airway mechanics, and/or other parameters. Gas parameters may include flow, (airway) pressure, humidity, velocity, acceleration, and/or other gas parameters. Output signals may convey measurements related to respiratory parameters. Sensor 142 may be in fluid communication with conduit 182 and/or subject interface appliance 184. Sensor 142 may generate output signals related to physiological parameters pertaining to subject 106. Parameters may be associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 12a (or of a device that pressure generator 12a is integrated, combined, or connected with) such as valve drive current, rotor speed, motor speed, blower speed, fan speed, or a related measurement and/or unit that may serve as a proxy for any of the parameters listed herein through a previously known and/or calibrated mathematical relationship. Sensed signals may include any information obtained by or extracted from fundamental relationships involving control parameters or surrogates.

The illustration of sensor 142 including two members in FIG. 1 is not intended to be limiting. In some hardware configurations, system 10 may use only one sensor 142. The individual sensor 142 may be located at or near subject interface appliance 184, or at other locations. In some hardware configurations, system may include a sensor 142 at or near output 141 of pressure generator 12a. The illustration of a sensor 142 at or near subject interface appliance 184 and a sensor 142 at or near output 141 of pressure generator 12a is not intended to be limiting. Resulting signals or information from one or more sensors 142 may be transmitted to processor 110, user interface 120, electronic storage 130, and/or other components of system 10. This transmission may be wired and/or wireless.

The one or more sensors 142 may be configured to generate output signals in an ongoing manner during a therapy session. This may include generating signals intermittently, periodically (e.g. at a sampling rate), continuously, continually, at varying intervals, and/or in other ways that are ongoing during at least a portion of the therapy session. For example, in some embodiments, the generated output signals may be considered as a vector of output signals, such that a vector includes multiple samples of information conveyed related to one or more gas parameters and/or other parameters. Different parameters may be related to different vectors. A particular parameter determined in an ongoing manner from a vector of output signals may be considered as a vector of that particular parameter.

Processor 110 of system 10 in FIG. 1 may be configured to provide information processing capabilities in system 10. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 may be configured to execute one or more computer program components. The one or more computer program components may include a control component 111 and/or other components. Processor 110 may be configured to execute control component 111 by software; hardware; firmware; some combination of software, hardware, and/or firmware; and/or other mechanisms for configuring processing capabilities on processor 110.

It should be appreciated that although control component 111 is illustrated in FIG. 1 as being co-located within a single processing unit, in embodiments in which processor 110 includes multiple processing units, control component 111 may be located remotely. The description of the functionality provided by control component 111 described herein is for illustrative purposes, and is not intended to be limiting, as control component 111 may provide more or less functionality than is described. For example, control component 111 may be eliminated, and some or all of its functionality may be incorporated, shared, integrated into, and/or otherwise provided by other components of system 10. Note that processor 110 may be configured to execute one or more additional components that may perform some or all of the functionality attributed below to one of control component 111.

Control component 111 of system 10 in FIG. 1 may be configured to determine one or more gas parameters, breathing parameters, and/or other parameters based on one or more of output signals generated by sensor(s) 142 and/or other information sources. Determinations may be based on measurements, calculations, estimations, approximations, previously known and/or calibrated mathematical relationships, and/or other ways to determine a parameter. The other information sources may include motor currents, motor voltage, motor parameters, valve parameters, and/or other sources. The determined parameters may include system parameters and/or controlled parameters, i.e. not just sensed signals.

Operation of control component 111 may be performed in an ongoing manner. The one or more gas parameter may include and/or be related to one or more of (peak) flow rate, flow rate, (tidal) volume, pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more gas parameters may be determined at different locations and/or positions within system 10, including within pressure generator 12a, at or near output 141 of pressure generator 12a, within subject interface 180, at or near the point of engagement between pressure generator 12a and subject interface 180, within conduit 182, at or near an input of conduit 182, at or near an output of conduit 182, within subject interface appliance 184, at or near an input of subject interface appliance 184, at or near an output of subject interface appliance 184, and/or at other locations and/or positions within system 10.

Control component 111 may derive one or more breathing parameters from one or more determined gas parameters and/or generated output signals. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters.

Control component 111 may be is configured to control operation of system 10 during a therapy session. Control component 111 may be configured to control pressure generator 12a to adjust one or more levels of gas parameters of the pressurized flow of breathable gas in accordance with one or more of a (respiratory) therapy regimen, based on target pressures, based on one or more algorithms that control adjustments and/or changes in the pressurized flow of breathable gas, and/or based on other factors and/or parameters as described herein. Control component 111 may be configured to control pressure generator 12a to provide the pressurized flow of breathable gas.

Figure 2:
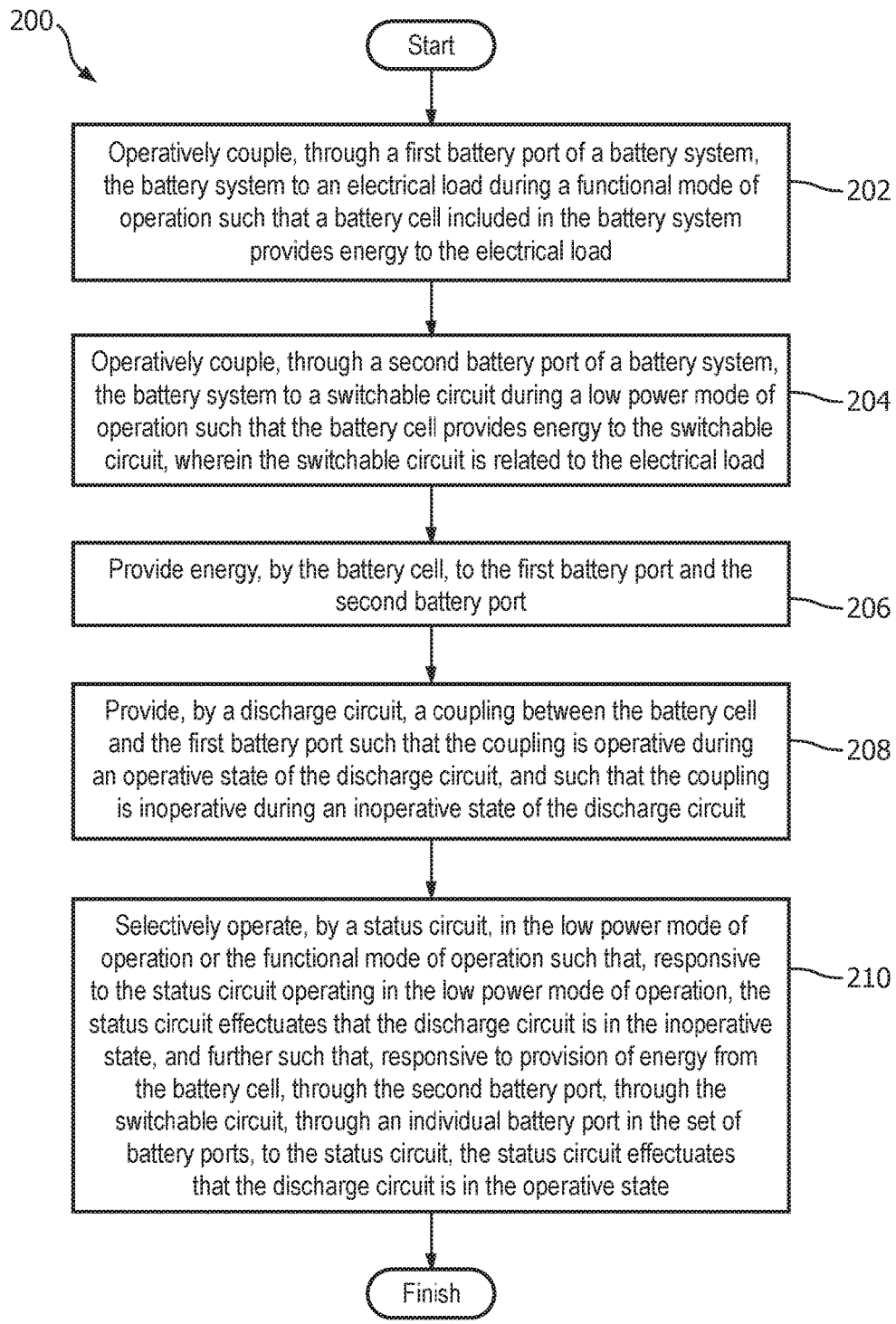
FIG. 2 illustrates a method for transitioning a battery system between a low power mode of operation and a functional mode of operation in accordance with one or more embodiments.

FIG. 2 illustrates a method 200 for transitioning battery system 11 between a low power mode of operation and a functional mode of operation. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in a battery system, one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, the battery system is operatively coupled to an electrical load during the functional mode of operation such that the battery cell provides energy to the electrical load. In some embodiments, operation 202 is performed by a first battery port the same as or similar to first battery port 19c (shown in FIG. 3A-3B and described herein).

At an operation 204, the battery system is operatively coupled to the switchable circuit during the low power mode of operation such that the battery cell provides energy to the switchable circuit. The switchable circuit is related to the electrical load. In some embodiments, operation 204 is performed by a second battery port the same as or similar to second battery port 19a (shown in FIG. 3A-3B and described herein).

At an operation 206, energy is provided by the battery cell, to the first battery port and the second battery port. In some embodiments, operation 206 is performed by a battery cell the same as or similar to battery cell 13 (shown in FIG. 3A-3B and described herein).

At an operation 208, a coupling is provided between the battery cell and the first battery port such that the coupling is operative during an operative state of the discharge circuit, and such that the coupling is inoperative during an inoperative state of the discharge circuit. In some embodiments, operation 208 is performed by a discharge circuit the same as or similar to discharge circuit 16 (shown in FIG. 3A-3B and described herein).

At an operation 210, a low power mode of operation or a functional mode of operation is selected. Responsive to selection of the low power mode of operation, the discharge circuit is in the inoperative state. Responsive to provision of energy from the battery cell, through the second battery port, through the switchable circuit, through an individual battery port in the set of battery ports, the discharge circuit is in the operative state. In some embodiments, operation 210 is performed by a status circuit the same as or similar to status circuit 15 (shown in FIG. 3A-3B and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A battery system constructed and arranged to control transitions between a low power mode of operation during which the battery system is configured to preserve energy and a functional mode of operation during which the battery system is configured to provide energy to one or more external circuits, the one or more external circuits being external to the battery system and including an electrical load and a switchable circuit, the battery system comprising:
 a set of battery ports configured to operatively couple the battery system to the one or more external circuits, wherein the set of battery ports includes a first battery port and a second battery port;
 a battery cell configured to provide energy to the first battery port and the second battery port, wherein the battery cell includes a first battery cell port;
 the first battery port configured to operatively couple the battery system to the electrical load during the functional mode of operation, wherein the first battery port is further configured to operatively couple the battery system to the electrical load during the provision of energy in the functional mode of operation;
 the second battery port configured to operatively couple the battery system to the switchable circuit during the low power mode of operation, wherein the second battery port is further configured to operatively couple the battery cell to the switchable circuit during the provision of energy in the low power mode of operation;
 a discharge circuit configured to provide a coupling between the first battery cell port and the first battery port, wherein the discharge circuit is further configured such that the coupling is operative during an operative state of the discharge circuit, and wherein the discharge circuit is further configured such that the coupling is inoperative during an inoperative state of the discharge circuit; and
 a status circuit configured to selectively operate in the low power mode of operation or the functional mode of operation, wherein:
  the status circuit is further configured to cause the discharge circuit to be in the inoperative state responsive to the status circuit operating in the low power mode of operation, the low power mode comprising a first low power sleep mode, wherein power consumption of the discharge circuit is reduced, and a second low power shutdown mode, wherein power consumption of the discharge circuit and the status circuit are reduced, and
  the status circuit is further configured to cause the discharge circuit to be in the operative state responsive to provision of energy from the battery cell, through the second battery port, through the switchable circuit, through an individual battery port in the set of battery ports, to the status circuit.

2. The battery system of claim 1, wherein the first battery port is further configured to operatively couple to the status circuit, wherein the provision of the energy through the second battery port, responsive to which the status circuit causes the discharge circuit to be in the operative state, is provided through the first battery port.

3. The battery system of claim 2, wherein the battery cell further includes a second battery cell port, wherein the status circuit is configured to selectively operate in the low power mode of operation in such a way that a coupling between the second battery cell port and the status circuit is inoperative.

4. The battery system of claim 1, further comprising a third battery port configured to indicate whether the electrical load is present or absent, wherein the status circuit is operatively coupled to the third battery port, and wherein the provision of the energy through the second battery port, responsive to which the status circuit causes the discharge circuit to be in the operative state, is furthermore coupled through the third battery port.

5. The battery system of claim 4, wherein the electrical load includes a ventilator, and wherein the switchable circuit is arranged such that, responsive to the switchable circuit being switched on, the second battery port is operatively coupled with the third battery port through the switchable circuit such that the battery cell provides energy, through the coupling, to the ventilator.

6. A method for controlling transitions of a battery system between a low power mode of operation during which the battery system preserves energy and a functional mode of operation during which the battery system provides energy to one or more external circuits, the one or more external circuits being external to the battery system and including an electrical load and a switchable circuit, the method being implemented in the battery system including a battery cell, a set of battery ports, a discharge circuit, and a status circuit, and wherein the set of battery ports includes a first battery port and a second battery port, the method comprising:
 operatively coupling, through the first battery port, the battery system to the electrical load during the functional mode of operation such that the battery cell provides energy to the electrical load;
 operatively coupling, through the second battery port, the battery system to the switchable circuit during the low power mode of operation such that the battery cell provides energy to the switchable circuit;
 providing energy, by the battery cell, to the first battery port and the second battery port;
 providing, by the discharge circuit, a coupling between the battery cell and the first battery port such that the coupling is operative during an operative state of the discharge circuit, and such that the coupling is inoperative during an inoperative state of the discharge circuit;
 responsive to the status circuit operating in the low power mode of operation, the status circuit causing the discharge circuit to be the inoperative state, the low power mode comprising a first low power sleep mode, wherein power consumption of the discharge circuit is reduced, and a second low power shutdown mode, wherein power consumption of the discharge circuit and the status circuit are reduced; and
 responsive to provision of energy from the battery cell, through the second battery port, through the switchable circuit, through an individual battery port in the set of battery ports, to the status circuit, the status circuit causing the discharge circuit to be the operative state.

7. The method of claim 6, further comprising: operatively coupling the first battery port to the status circuit, wherein the individual battery port is the first battery port.

8. The method of claim 7, further comprising:
 providing, through a battery cell port of the battery cell, status information pertaining to one or more status parameters of the battery cell to the status circuit in the functional mode of operation;
 receiving and processing, by the status circuit, the status information, wherein selectively operating, by the status circuit, in the low power mode of operation includes causing the status circuit reversibly to cease processing of the status information.

9. The method of claim 6, wherein the set of battery ports further includes a third battery port that indicates whether the electrical load is present or absent, the method further comprising: operatively coupling the status circuit to the third battery port, wherein the individual battery port is the third battery port.

10. The method of claim 9, wherein the electrical load includes a ventilator, the method further comprising: arranging the switchable circuit such that, responsive to the switchable circuit being switched on, the second battery port is operatively coupled with the third battery port through the switchable circuit such that the battery cell provides energy, through the coupling, to the ventilator.

11. A battery system constructed and arranged to control transitions between a low power mode of operation during which the battery system preserves energy and a functional mode of operation during which the battery system provides energy to one or more external circuits, the one or more external circuits being external to the battery system and including an electrical load and a switchable circuit, the battery system comprising:
a set of coupling means for operatively coupling the battery system to the one or more external circuits, wherein the set of coupling means include a first coupling means and a second coupling means;
energy means for providing energy to the first coupling means and the second coupling means;
the first coupling means for operatively coupling the battery system to the electrical load during the functional mode of operation such that the energy means provides energy to the electrical load;
the second coupling means for operatively coupling the battery system to the switchable circuit during the low power mode of operation such that the energy means provides energy to the switchable circuit;
discharge means for providing a coupling between the energy means and the first coupling means such that the coupling is operative during an operative state of the discharge means, and such that the coupling is inoperative during an inoperative state of the discharge means;
status means for selectively operating in the low power mode of operation or the functional mode of operation such that:
responsive to the status means operating in the low power mode of operation, the status means is configured to cause the discharge means to be in the inoperative state, the low power mode comprising a first low power sleep mode, wherein power consumption of the discharge means is reduced, and a second low power shutdown mode, wherein power consumption of the discharge means and the status means are reduced, and
responsive to provision of energy from the energy means, through the second coupling means, through the switchable circuit, through an individual coupling means in the set of coupling means, to the status means, the status means is configured to cause the discharge means to be in the operative state.

12. The battery system of claim 11, wherein the first coupling means is further configured to operatively couple with the status means; wherein the provision of energy from the energy means to the status means is provided through the first coupling means.

13. The battery system of claim 12, wherein the energy means is further configured to provide status information to the status means in the functional mode of operation, wherein the status means is further configured to receive and process the status information, wherein the status means is further configured to reversibly cease processing of the status information in the low power mode of operation.

14. The battery system of claim 11, wherein the set of coupling means further includes a third coupling means that indicates whether the electrical load is present or absent, wherein the third coupling means is configured to operatively couple with the status means, and wherein the provision of energy from the energy means to the status means is provided through the third coupling means.

15. The battery system of claim 14, wherein the electrical load includes a medical device, wherein the switchable circuit is arranged such that, responsive to the switchable circuit being switched on, the second coupling means is operatively coupled with the third coupling means through the switchable circuit such that the energy means provides energy, through the coupling, to the medical device.

* * * * *